United States Patent
Radcliffe

(10) Patent No.: US 7,305,886 B2
(45) Date of Patent: Dec. 11, 2007

(54) NOISE DETECTING APPARATUS

(75) Inventor: Clark J. Radcliffe, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 255 days.

(21) Appl. No.: 11/147,400

(22) Filed: Jun. 7, 2005

(65) Prior Publication Data

US 2006/0000282 A1 Jan. 5, 2006

Related U.S. Application Data

(60) Provisional application No. 60/577,939, filed on Jun. 7, 2004.

(51) Int. Cl.
*G01N 29/07* (2006.01)
*G01S 11/14* (2006.01)
*G10K 11/00* (2006.01)

(52) U.S. Cl. ............................ 73/647; 73/597; 367/99; 367/127; 381/71.1

(58) Field of Classification Search .................. 73/647, 73/646, 587, 597, 599, 602; 381/71.1, 71.2; 342/52, 54, 56; 367/99, 118, 127, 189; 702/189, 702/191–195
See application file for complete search history.

(56) References Cited

U.S. PATENT DOCUMENTS 3,844,175 A * 10/1974 Hixson ........................ 73/647
4,179,937 A * 12/1979 Koblanski ..................... 73/646
4,257,273 A * 3/1981 Knowd .......................... 73/647
4,563,274 A * 1/1986 Rothon et al. ............... 210/101
4,575,829 A * 3/1986 Duhe ............................ 367/129
4,581,726 A * 4/1986 Makino et al. ................ 267/99
4,739,860 A * 4/1988 Kobayashi et al. .......... 181/123
5,636,287 A * 6/1997 Kubli et al. ................ 381/71.2
6,084,973 A * 7/2000 Green et al. ................... 381/92
6,434,239 B1* 8/2002 DeLuca ...................... 381/71.2
2003/0154054 A1* 8/2003 Charette et al. ............. 702/188
2005/0041529 A1* 2/2005 Schliep et al. ................ 367/99
2006/0198537 A1* 9/2006 Moorer ........................ 381/92

OTHER PUBLICATIONS

Document related to use entitled "Testing on Higgin's Lake," C. Radcliffe, Jun. 20, 2003, 2 pgs.
"Boat Noise Abatement Project Moves Forward, Sound Gun Demonstration Successful at Higgins Lake Tests," C. Radcliffe et al., The Michigan Riparian, vol. 38, No. 3, Aug. 2003, pp. 8-11.

* cited by examiner

*Primary Examiner*—Hezron Williams
*Assistant Examiner*—Jacques M. Saint-Surin
(74) *Attorney, Agent, or Firm*—Harness, Dickey & Pierce, P.L.C.

(57) ABSTRACT

An accurate measure of normally operating noise is required for a useful noise measurement system. A device is needed to make a representative measure of the boat's acoustic power using measured boat sound level with integrated corrections for sensed distance to the boat and measured ambient sound level. This device needs to make this measurement process invisible, automatic, and accurate from a law enforcement point of view.

21 Claims, 24 Drawing Sheets

SAE J34 Test Layout

Figure 1: SAE J34 Test Layout

Figure 2: Sound Propagation from a Point Source

Figure 3: Sound Propagation from an Infinite Plane

Figure 4: Sound Propagation Test Setup

Figure 5: Test Data

Figure 6: Sound Level Decay

Figure 7: Sound Level Compensation C

Figure 8: Polar Response Pattern of the Audio-Technica AT815b

Figure 10: MX636 dB Conversion Circuit
(Maxim (1998). Figures 5 and 10)

Figure 11: Microphone Amplifier Circuit

Figure 12: ADC0831 A/D Converter Circuit

Figure 13: Noise Gun Program Flowchart

Figure 15: Data from the First Anechoic Test for White Noise

Figure 16: Data from the Second Anechoic Test for White Noise

Figure 17: Polar Response of (AT815-b) at 250 Hz Octave Band

Figure 18: Summary of 27 Noise Gun Measurements

Figure 19: Lake Test data with the dB decay level altered

Figure 20: dB decay level altered for two cases

Figure 22: Spherical Sound Propagation

NOISE DETECTING APPARATUS

CROSS-REFERENCE TO RELATED APPLICATIONS

This claims the benefit of U.S. Provisional Application No. 60/577,939, filed on Jun. 7, 2004 The disclosure of the above application is incorporated herein by reference

FIELD OF THE INVENTION

The present invention relates to noise measurement equipment and, more particularly, to equipment configured to repeatably measure noise from a moving object at variable distance.

BACKGROUND & SUMMARY OF THE INVENTION

Excessive noise levels on lakes are the source of many community problems. Given the increasing numbers of boats on lakes, shoreline residents who wish to maintain a peaceful environment have a vested interest in controlling noise pollution.

Current standards for measuring noise levels of boats are written in various State Acts. The current standards often cited are testing procedures SAE J2005 (SAE 1991b) and SAE J1970 (SAE 1991a), which tend to discourage the state law officials who try to apply and enforce them. The SAE J2005 standard requires that the target boat be tethered to either another boat or a dock. The engine motor is set to idle, and the measurement is taken three feet away. This requires extraordinary cooperation not only from the vehicle operator, but also from all other boats in the immediate environment. The SAE J1970 standard is a shoreline-based measurement of the boat noise. The measurement is taken from the shore, as long as the boat is not within 30 seconds of leaving or returning to shore. SAE J1970 can only be used when the offending boat is alone on the water and near to shore, thus making citation of the offending vehicle operator difficult.

The J2005 standard is intended as a stationary test for motorboats. This test is designed to determine whether a boat's muffling system is adequate to reduce the sound power of the boat. The basic procedure is as follows:
  The boat must be docked or tied to another boat.
  The boat must be in a neutral gear, or at its lowest idle speed possible.
  The microphone must be placed 1.2 to 1.5 m (4 to 5 ft) above the water, and no closer than 1 m (3.3 ft) from the boat itself.
  The background noise level must be at least 10 dB lower than the level of the boat.

The J2005 test was designed mainly because stationary tests are easier to conduct than tests performed while boats are in motion. There are many problems with stationary tests, however. The process of identifying a noisy boat, chasing it down, lashing it to a police boat, and then administering the test is long and cumbersome, besides being impossible to conduct in rough water. Furthermore, newer boats have a "captain's choice" exhaust, which allows boat operators to switch between underwater exhaust and unmuffled air exhaust. Obviously, when a test is administered, a captain would switch to the quieter underwater exhaust system. The J2005 test simply does not address the problem of unreasonably noisy boats on the water.

The J1970 standard is meant to test the sound level of boats as perceived on the shoreline by riparian owners, the originators of most of the complaints. The basic procedure in this test is:
  The measurement must be taken either on shore or on a dock not more than 6 m (20 ft) from shore.
  The microphone must be placed 1.2 to 1.5 m (4 to 5 ft) above the water.
  There is no distance requirement to the target boat. The boat must not be measured 30 seconds after it launches or its last 30 seconds coming into the dock.
  The background level must be at least 10 dB lower than the level of the boat.

Theoretically, the use of a shore measurement should be enough to satisfy shoreline residents regarding boat noise. However, there are problems with this test as well. First of all, it is not easy to perform unless there is only one boat on the water, which never happens in the busy summer season. Secondly, the noisy boat can be over a mile away, but this test is impossible to conduct at such a distance. These tests, if enforcement were easy to carry out, would alleviate some of the noise problem. However, the many intricacies of measurement procedures, coupled with the variables that affect noise level which are not taken into account, produce loopholes so that citations can be challenged successfully in the court. Therefore the J1970 and J2005 standards are inadequate for enforcing a noise measurement standard for boats in-use on the water.

The SAE J34 standard (SAE 2001) is referred to in the laws of fourteen states. It seeks to provide a comprehensive test to determine the maximum sound level of the boat in use. A summary of this test is as follows:
  A test site must be created as shown in FIG. 1.
  The boat must pass within of 3 m (10 ft) on the outside of the buoys.
  The boat must be at +/−100 rpm of its full throttle rpm range.
  The microphone must be placed 1.2 to 1.5 m (4 to 5 ft) above the water, and no less than 0.6 m (2 ft) above the dock surface.
  The background level must be at least 10 dB lower than the level of the boat.
  The wind speed must be below 19 km/h (13 mph).
  The peak reading as the boat completes the course shall be recorded.
  Two readings will be made for each side of the boat.

The J34 standard successfully measures the peak in-use noise level of the boat as it traverses the course. However, the complexity of setting up a course, and the range of variables which must be recorded, necessitate that there must be an officer in the boat as well as on the dock. It requires skillful piloting, extremely calm conditions, and patient and qualified officers to administer the test. This standard is meant as a way for boat manufacturers to certify their boats are compliant with noise standards, rather than as an on-lake test for noisy boaters. The J34 test provides a measured value that is related to the sound power of the boat. However, the difficulty in administering this test limits its usefulness for enforcement of noise statues.

The solution to the noise standards enforcement problem lies in the creation of a noise measurement standard, which allows the accurate measurement of the in-use noise level of a boat or vehicle. The goal of the standard is to compute a value representative of the acoustic power of the noise source without requiring operator cooperation. Enforcing this standard would require a device that would compute a value representative of the noise level of a boat unaffected by distance, background noise level of other boats, and weather. In order to compute this representative value of acoustic power, a model of sound propagation is needed. With this model, and a distance measurement, the point sound pressure (dB) measurement can be related to the sound power of the boat. A measure of the background noise level is also needed so that the influence of other noise sources can be removed from the measurement. The purpose of this work is to create such a "sound measuring device." This device, coupled with redrafted statues, would finally allow law enforcement officers to enforce a reasonable noise level standard not only for boats, but for ATV's, snowmobiles, and other vehicles.

A noise measurement device that is more advanced than a standard noise meter is required by the new standard. The meter will need to output a predicted minimum possible sound level of the boat at a standard distance away, after compensating for various possible measurement errors including, but not limited to, background noise and noise propagation characteristics. This will allow for measurements to be compared to other boat measurements no matter how far the meter operator is from the boat. Sound propagation and measurement techniques need to be reviewed in order to make this prediction.

The noise measurement device will need to do these predictions in an invisible manner from the operator. The corrected noise level at a standard distance away will eliminate the problems of reliability of the measurement. The integration of this procedure into a single electronic instrument will eliminate the difficulty in use that plagues the other standards. With this device, the new noise measurement standard can be used easily for law enforcement.

The noise measurement device utilizes how sound propagates over water for noise level calculations. As such, it is an object of the invention to measure the sound level at the position of the observer, and convert it into what the equivalent sound level would be at a standard distance from the source. Two models of how sound propagates are used to develop the noise measurement device, a point source and an infinite plate source. The affect of background noise on the measurement of sound level is determined.

Spherical sound propagation is one way to idealize the acoustic propagation field produced by a boat. The point produces a level of acoustic power, which then propagates uniformly away from the point over a sphere. The acoustic power is assumed constant at any distance from the point. The energy is spread over the sphere of radius r from the sound origin. This derivation is based on standard sound propagation theory.

The acoustic intensity (I) is an energy flux (W/m$^2$). The acoustic power ($P_{source}$) is the integral of that flux over some sphere (radius r, surface area A) surrounding the source, $$P_{source} = \int I dA = I(4\pi r^2) \quad (1)$$

Acoustic intensity is related to the square of the acoustic pressure (p), where $\rho$ is the air density, and c is the speed the wave (sound), $$I = \frac{p^2}{\rho c} \quad (2)$$

Relating the acoustic power to the acoustic pressure with (1) and (2), $$\frac{p^2}{\rho c} = \frac{P_{source}}{4\pi r^2} \quad (3)$$

The relationship between the ratios of pressures to the ratio of distances is determined using:

$$\frac{p_2}{p_1} = \frac{\sqrt{\rho c(P_{source})/4\pi r_2^2}}{\sqrt{\rho c(P_{source})/4\pi r_1^2}} = \frac{r_1}{r_2} \quad (4)$$

Sound pressure level is a function of acoustic pressure. It is specified in decibels, defined as $$SPL = 20\log_{10}\left(\frac{p}{p_{ref}}\right) \quad (5)$$

where $p_{ref}$ is a reference pressure ($2\times10^{-5}$ Pa),

The change in sound pressure level for two points is $$\Delta SPL = SPL(r_2) - SPL(r_1) \quad (6)$$
$$= 20\log_{10}\left(\frac{p_2}{p_{ref}}\right) - 20\log_{10}\left(\frac{p_1}{p_{ref}}\right)$$
$$= 20\log_{10}\left(\frac{p_2}{p_1}\right)$$
$$= 20\log_{10}\left(\frac{r_1}{r_2}\right)$$

For a doubling of distance, $r_1=1$ and $r_2=2$, the $\Delta SPL$ is $-6$ dB.

An infinite plane source is the other limiting case of a boat sound propagation field. This approximation can be used very close to the boat. In this case, an infinite wall radiates sound at the same intensity at every point on the wall. Since the sound wave travels linearly away from the wall and does not expand, the sound intensity from an infinitesimal patch radiates over a rectangle. The acoustic power remains constant since the area is constant, and therefore the sound level at any point away from the wall is constant.

The acoustic intensity (I) is an energy flux (W/m$^2$). The acoustic power ($P_{source}$) is the integral of that flux $$P_{source} = \int I dA = I(A) \quad (7)$$

Acoustic intensity is related to the square of the acoustic pressure.

$$I = \frac{p^2}{\rho c} \quad (8)$$

Relating the acoustic power to the acoustic pressure with (7) and (8), $$\frac{p^2}{\rho c} = \frac{P_{source}}{A} \qquad (9)$$

The relationship between the ratio of pressures to the ratio of areas is determined by:

$$\frac{p_2}{p_1} = \frac{\sqrt{\rho c(P_{source})/A_2}}{\sqrt{\rho c(P_{source})/A_1}} = \frac{A_1}{A_2} \qquad (10)$$

Since the surface is infinite, the acoustic energy radiates outward into the same area at every radius from the surface. So $A_1 = A_2$, and $$\frac{p_2}{p_1} = \frac{A}{A} = 1 \qquad (11)$$

The change in sound pressure level for two points is $$\begin{aligned}\Delta SPL &= SPL(r_2) - SPL(r_1) \\ &= 20\log_{10}\left(\frac{p_2}{p_{ref}}\right) - 20\log_{10}\left(\frac{p_1}{p_{ref}}\right) \\ &= 20\log_{10}\left(\frac{p_2}{p_1}\right) \\ &= 20\log_{10}(1) = 0 \end{aligned} \qquad (12)$$

The change in sound pressure level, $\Delta SPL$, is always 0 dB.

The National Marine Manufacturers Association (NMMA 1987) set out to measure the sound propagation field from motorboats. A boat is neither a point source nor an infinite wall source; its decay is somewhere between these two cases. These tests measured the propagation decay of a group of actual boats. Sound level meters were placed on poles at 50, 75, 100, and 200 feet away from a straight buoy course that the boat traversed. This allowed simultaneous readings of the boat noise at different distances. This test was conducted for a wide range of boats (with horsepowers from 10 to 370) in a single set of conditions. FIG. 5 displays the data gathered in this experiment.

The Marine Manufacturers Association study determined experimentally that on average boats had a 5 dB drop per doubling of distance. Further testing is needed to determine the average sound level decay for most watercraft, since this set of testing was not as rigorous and complete as is needed to stand up to court challenges. The data shows that most vehicles exhibited a decay value of between 4 and 6 dB per doubling of distance.

FIG. 6 displays the differences between various decay values. If a boat noise level is 85 dB at 200 feet, which model used would affect your prediction of the sound level at 50 feet. If, for example, the model assumed that sound decayed at 4 dB per doubling of distance, the model would predict that the boat would be 93 dB at 50 feet. If the model assumed a 6 dB drop, the model would predict 97 dB at 50 feet. It is important to determine what this decay value is in order for the device to make an accurate prediction.

Background noise is key to making a precise noise measurement. A noise source can only be measured when it is louder than the surrounding noise level. Even when the source is above the background, the reading taken from a source is a combination of the source noise and the background noise. The SAE noise standards only allow measurements when the measured source is 10 dB higher than the background. Because of this, the sound measuring device must correct for the background sound level.

Since the noise reading is a linear combination of the sound intensities from the background and the source, we can subtract the background contribution. The total mean squared measured sound $y_m$ is the sum of the source $y_s$ and background noise $y_b$, for a broadband random noise, $$y_m = y_s + y_b \qquad (13)$$

This total measured sound $Y_m$ is expressed on a decibel (dB) scale as $$Y_m = 20\log_{10}(y_m) = 20\log_{10}(y_s + y_b) \qquad (14)$$

where the measured background level $Y_b$ $$Y_b(dB) = 20\log_{10}(y_b) \qquad (15)$$

and the desired sound source level $Y_s$ $$Y_s(dB) = 20\log_{10}(y_s) \qquad (16)$$

Solving for the source and background levels in (13) yields $$y_b = 10^{(Y_b/20)} \qquad (17)$$

$$y_s = 10^{(Y_s/20)} \qquad (18)$$

These results can now be substituted into (16) and (13) to solve for the source pressure $y_s$ and source level in decibels $$\begin{aligned}Y_s(dB) &= 20\log_{10}[y_s] \\ &= 20\log_{10}[y_m - y_b] \\ &= 20\log_{10}[10^{(Y_m/20)} - 10^{(Y_b/20)}]\end{aligned} \qquad (19)$$

Rearranging (19) to collect terms and compute compensation in dB, $$\begin{aligned}Y_s(dB) &= 20\log_{10}\left[(10^{(Y_m/20)})\left(1 - \frac{10^{(Y_b/20)}}{10^{(Y_m/20)}}\right)\right] \\ &= 20\log_{10}(10^{(Y_m/20)}) + 20\log_{10}(1 - 10^{((Y_b - Y_m)/20)})\end{aligned} \qquad (20)$$

This compensation equation (20) can now be written as $$Y_s(dB) = Y_m + C \qquad (21)$$

where the compensation $C = 20\log_{10}(1 - 10^{[(Y_b - Y_m)/20]})$. Because the argument of the log function is always less than 1, the compensation C will always be negative.

The graph shows the required correction given the difference between the measured noise source value and the background noise. When the difference between the measurement and the background is 10 dB, the measured value is about 3.3 dB too high. Thus, if the background is 70 dB, and the measured source value is 80 dB, the real source level is about 76.7 dB. This correction is not valid when the source sound level and the background sound level are very close in value.

Directional measurement is an important factor in the measurement of boat or vehicle noise. The sound measurement must discriminate between the target object and other objects in the vicinity. There are two types of microphones that are generally used for directional pickup—a parabolic microphone or a shotgun microphone.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

Figure 9:
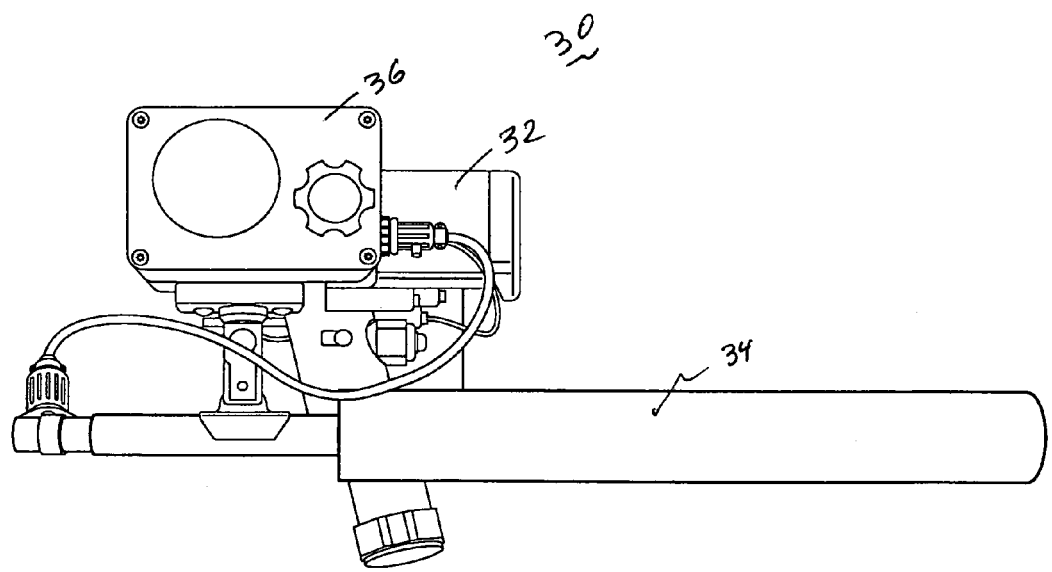
FIG. 9 is a noise level meter according to the teachings of the present invention.

The noise detection apparatus 30 according to the teachings of the present invention shown in FIG. 9. The system utilizes a range finder 32, a microphone 34, and a controller 36. Controller 36 utilizes output signals from range finder 32 in the form of range values in combination with received sounds detected by microphone 34 from a noise producing target 38 to calculate the amount of noise being produced at the target. It is envisioned noise producing target 38 can be a movable vehicle such as a boat or automobile. Range finder 32 is configured to transmit and receive a reflected signal using known propagation principles to calculate the distance to the target. It is envisioned range finder 32 can use a pulse laser, radar, or ultrasound. Microphone 34 is preferably a shotgun microphone having known properties which can be an Audio-Technica model AT815b. At moderate frequencies, this microphone provides up to a 20 dB gain for on-axis measurements. Disposed between microphone 34 and controller 36 is an optional amplifier 40 and analog to digital converter 42. At a level of 100 dB along the axis of the microphone, the microphone generates a voltage of $$100 \text{ dB } SPL=(2 \text{ Pa})(11.2 \text{ mV/Pa})=22.4 \text{ mV} \quad (22)$$

In one embodiment of the invention, a Contour Laser-Rangefinder XLR is used as rangefinder 32 to handle the distance measurement. Rangefinder 32 device sends out a pulsed infra-red laser and measures the amount of time it take for the beam to return the reflection of the beam, at a resolution of 0.1 foot. The time it takes for the beam to return, multiplied by the speed of light (approximately 983,571,056 feet per second), is twice the distance to the target. This means that for a 10 foot measurement, rangefinder 32 would measure a time of $2\times10^{-8}$ seconds. The difference between a 10 foot measurement and a 10.1 foot measurement would be $2\times10^{-10}$ seconds. The ease of use and the built-in computer interface made this device an easy choice for the prototype. However, in a production model of the boat sound measuring device, it is envisioned a customized version would be designed to remove much of the bulk of the current device.

Noise measuring device controller 36 can be a basic stamp microcontroller. This controller 36 takes sound level and distance inputs, computes all relevant corrections, and controls the output displays as specified in its custom program. It is interfaced with analog circuitry that does the signal processing. The use of a microcontroller allows controller 36 simple software updates to change the operation of the device.

Figure 10:
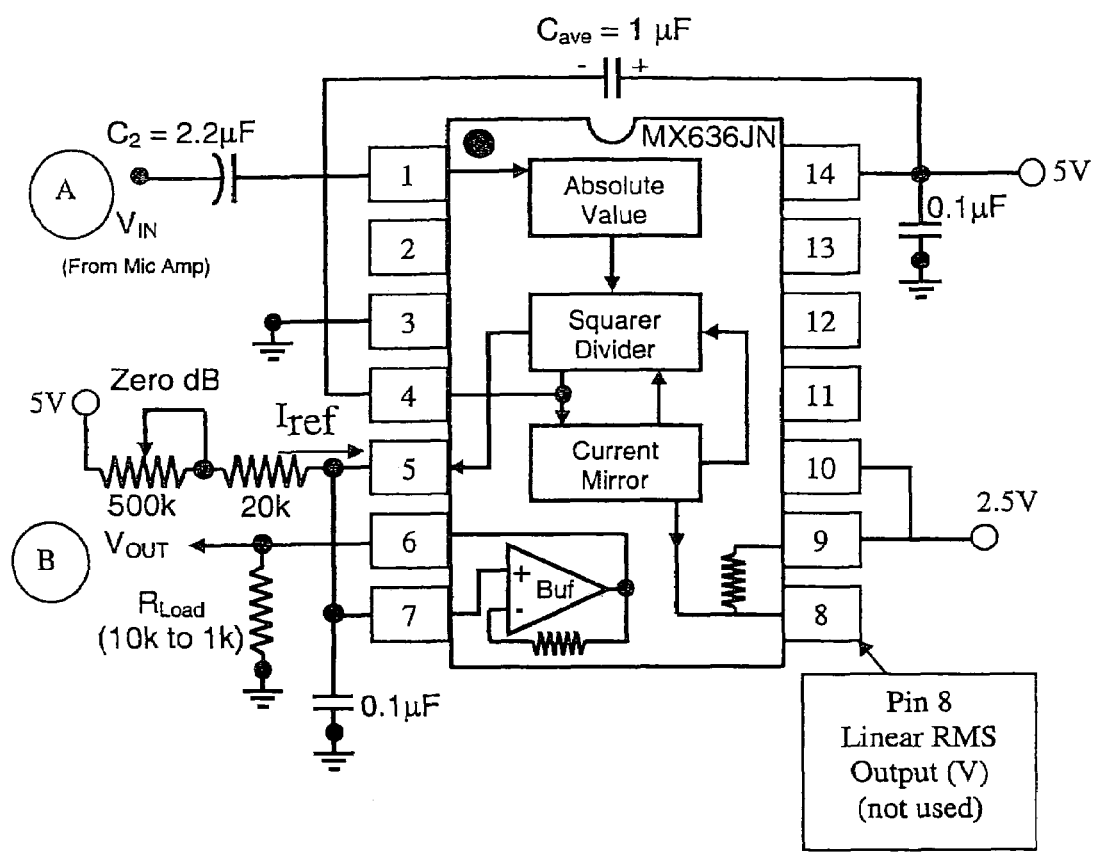
FIG. 10 is a MX636 dB conversion circuit used in the noise meter shown in FIG. 9.

The signal into A in FIG. 10 is from microphone 34 and is an AC signal. In order to measure this signal, it must be rectified into a DC level. This DC level can be easily measured by digital converter 42 that converts the analog DC voltage into a digital number. A Maxim MX636 chip takes the linear AC input from the microphone stages and converts it to a DC voltage that is proportional to the dB level of the input signal (log scale). This part of the circuit is a standard operating configuration recommended by the manufacturer, Maxim.

The input signal must first be filtered of low frequency noise. $C_2$ forms a high pass filter with the input resistance of 6.7 kΩ for the MX636 to remove low frequency bias. In order to be converted from an AC signal to a DC signal, the signal frequency must be above 10.8 Hz.

The time period over which the RMS value is measured is defined by the averaging capacitor, $C_{ave}$. $C_{ave}=1$ μF corresponds to a settling time of 115 msec at an input voltage level of 100 mV. Smaller input voltages take longer to settle. At an input of 1 mV, the settling time is ten times longer (about 1.1 seconds). The RMS calibration on Pin 5 is −3 mV/dB. As the input RMS level changes by 50 dB, the output voltage (Pin 5) should change by −150 mV from the 0 dB reference value set by the variable resistor on the pin.

Figure 11:
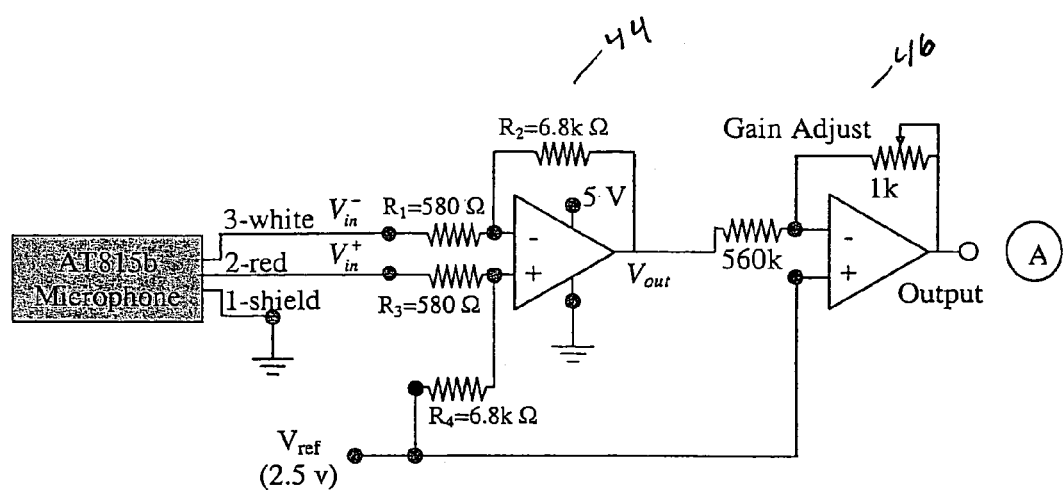
FIG. 11 is a microphone amplifier circuit used in the noise meter shown in FIG. 9.
Figure 12:
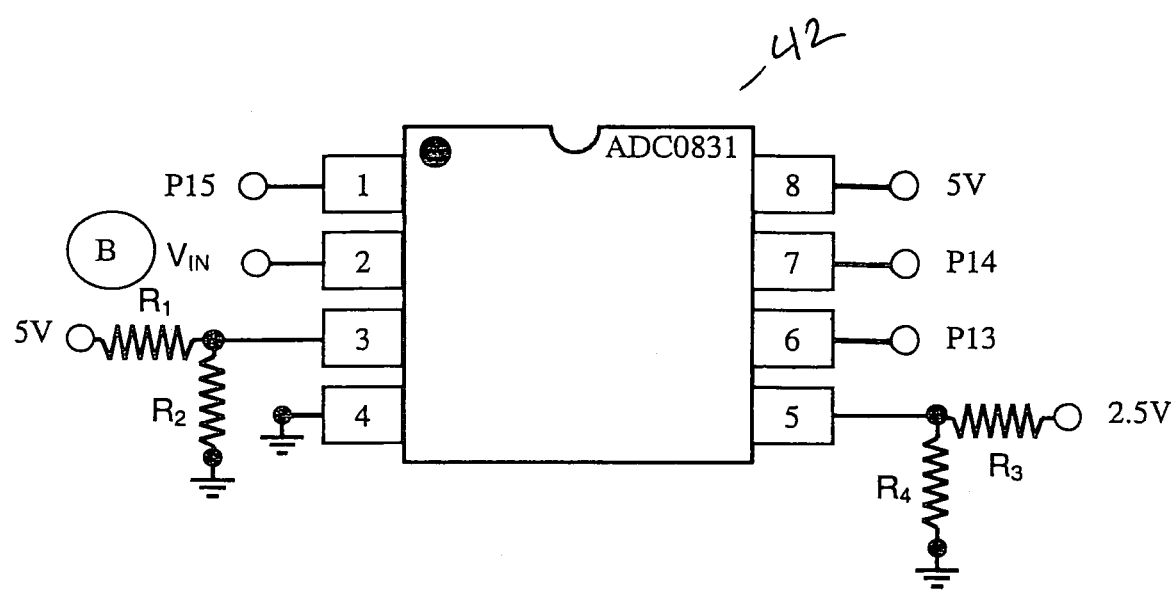
FIG. 12 is an ADC0831 A/D converter circuit used in the noise meter shown in FIG. 9.

Microphone amplifier circuit 40 in FIG. 11 is needed to interface low level shotgun microphone 34 output with the dB log measuring circuit (MX636). The input impedance of the circuit needs to match the output impedance of the microphone. The output needs to match the input requirements of the MX636 chip. This requirement is a voltage change of 0-200 mV RMS over the full range of sound inputs. The 200 mV swing must occur around a bias of 2.5V.

Optionally, microphone 34 can be a parabolic microphone using a large parabolic reflector to reflect sound waves into the microphone. This reflector only reflects wavelengths of sound less than the radius of the dish. This requirement means that for a frequency of 1000 Hz, the radius of the reflector must be at least 0.33 meters. For a frequency of 100 Hz, the microphone must have a radius of over 3.3 meters. This type of microphone 34 provides 20-40 dB of discrimination between the target and other noise sources in the general direction of the target.

Figure 1:
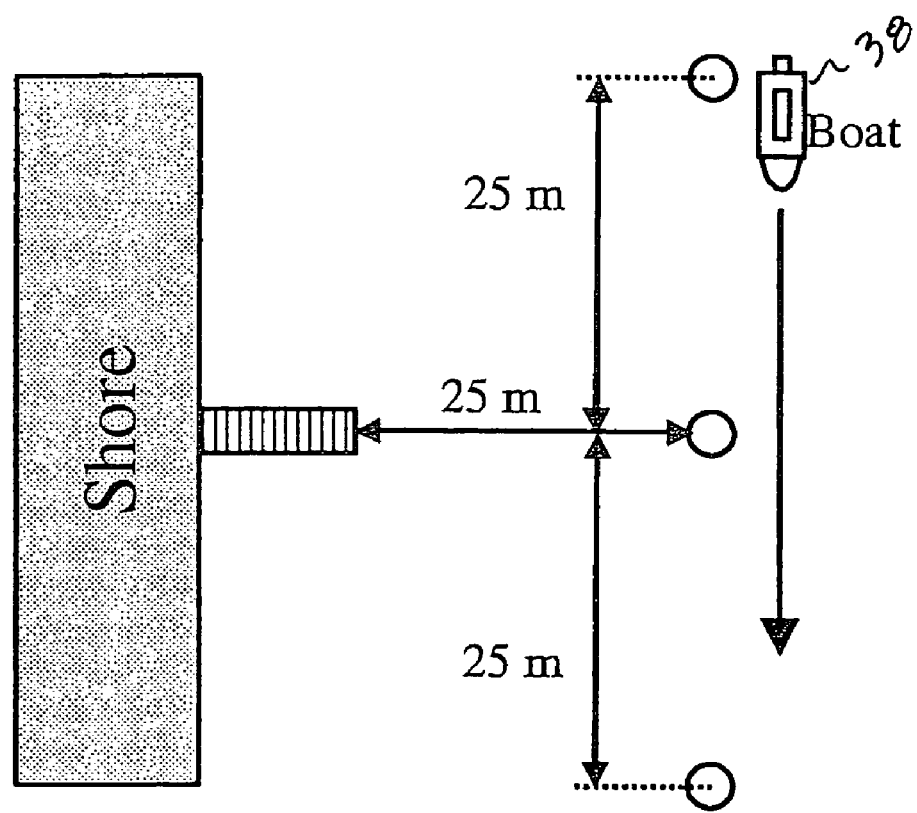
FIG. 1 is a SAE J34 Test Layout.
Figure 2:
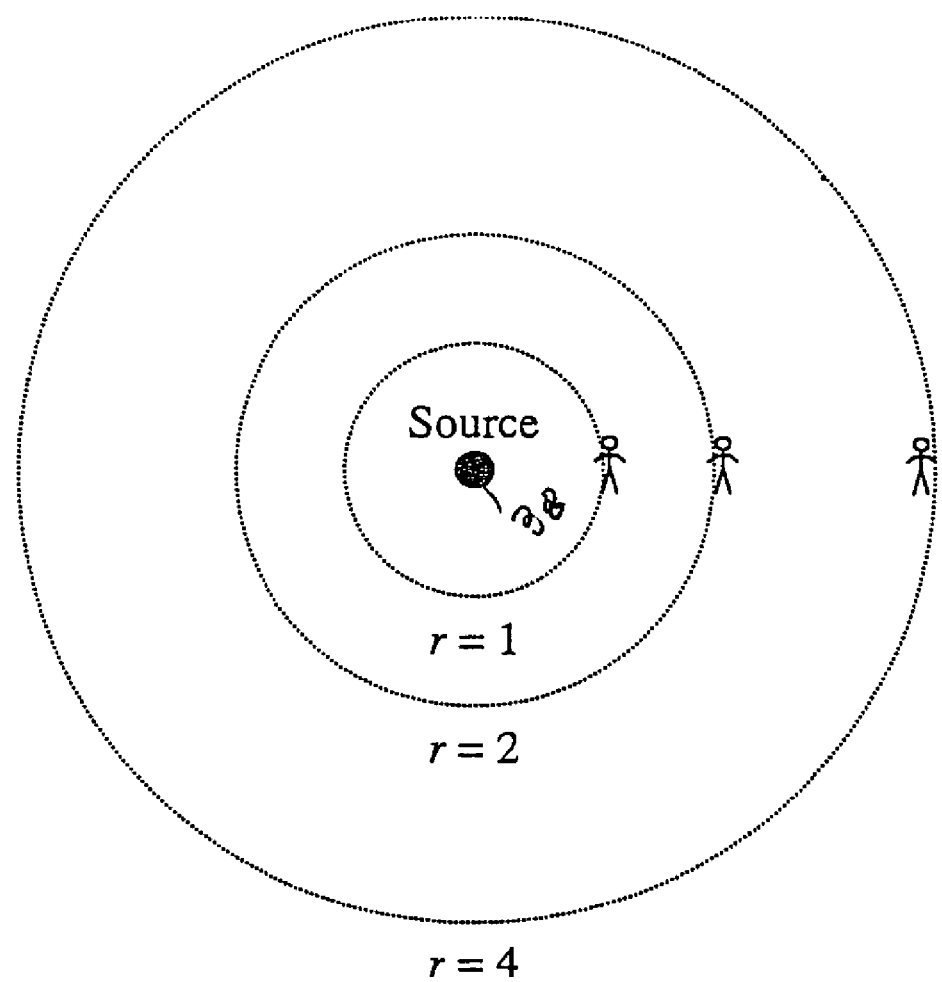
FIG. 2 is a sound propagation from a point source.
Figure 3:
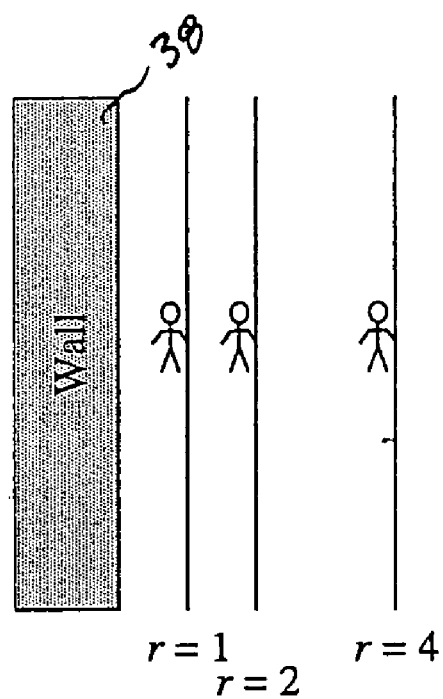
FIG. 3 is a sound propagation from an infinite plane.
Figure 4:
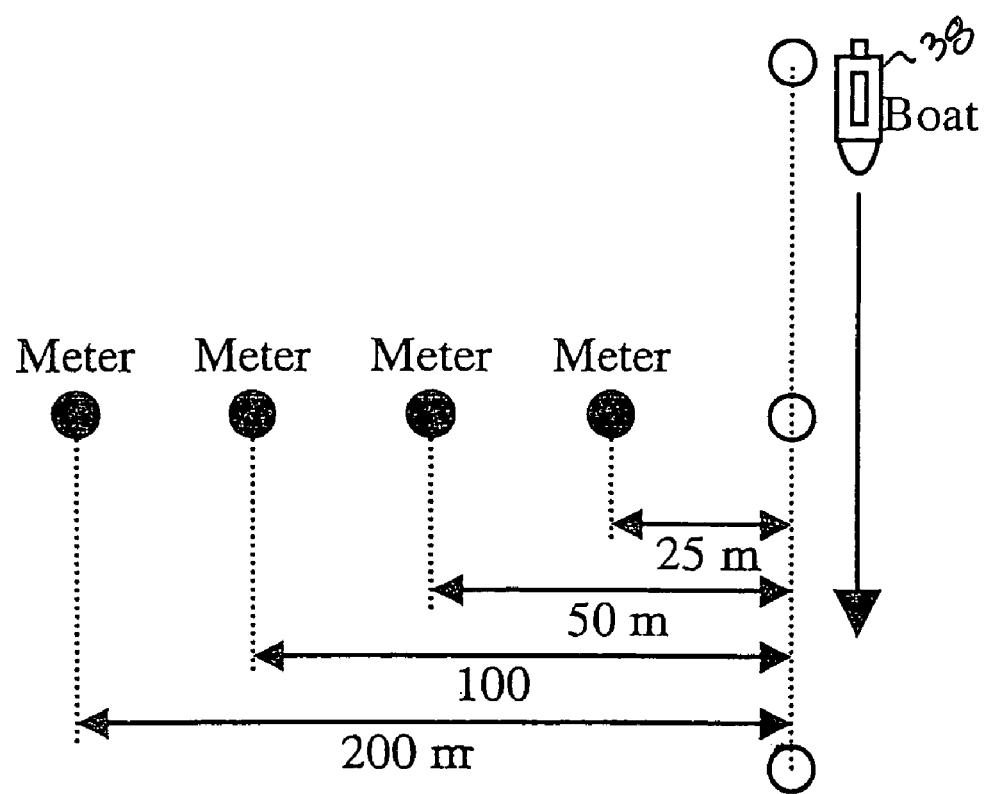
FIG. 4 is a sound propagation from test setup.
Figure 5:
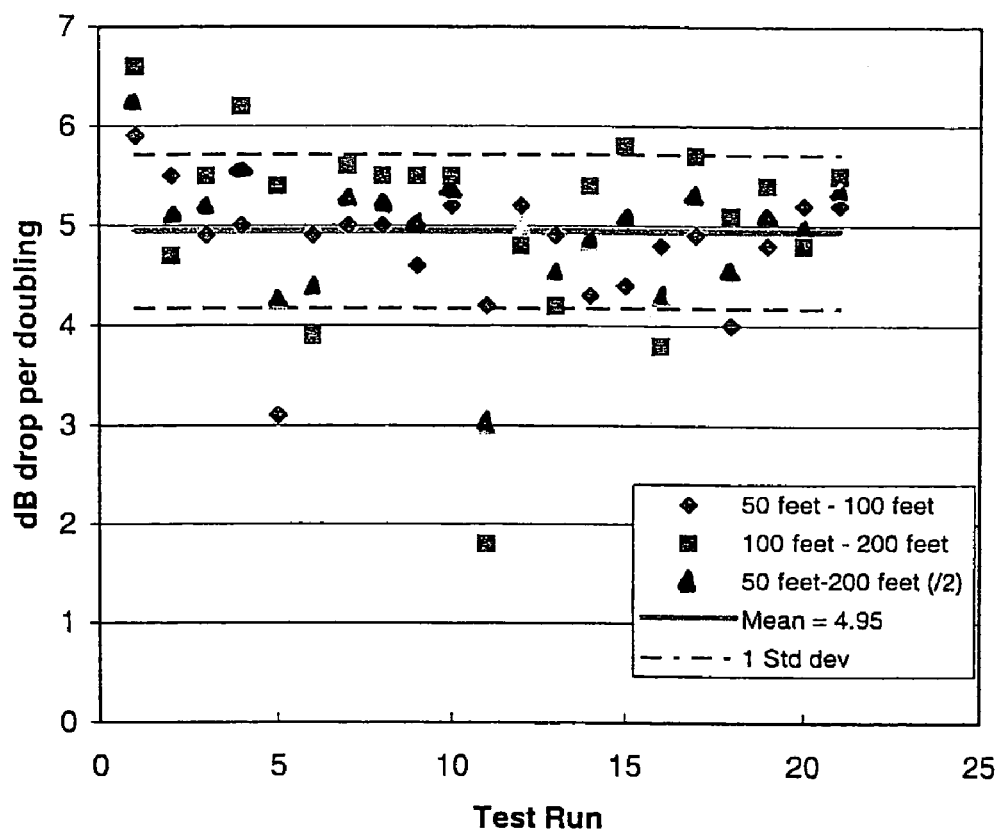
FIG. 5 is the National Marine Manufacturers Association Test Data.
Figure 6:
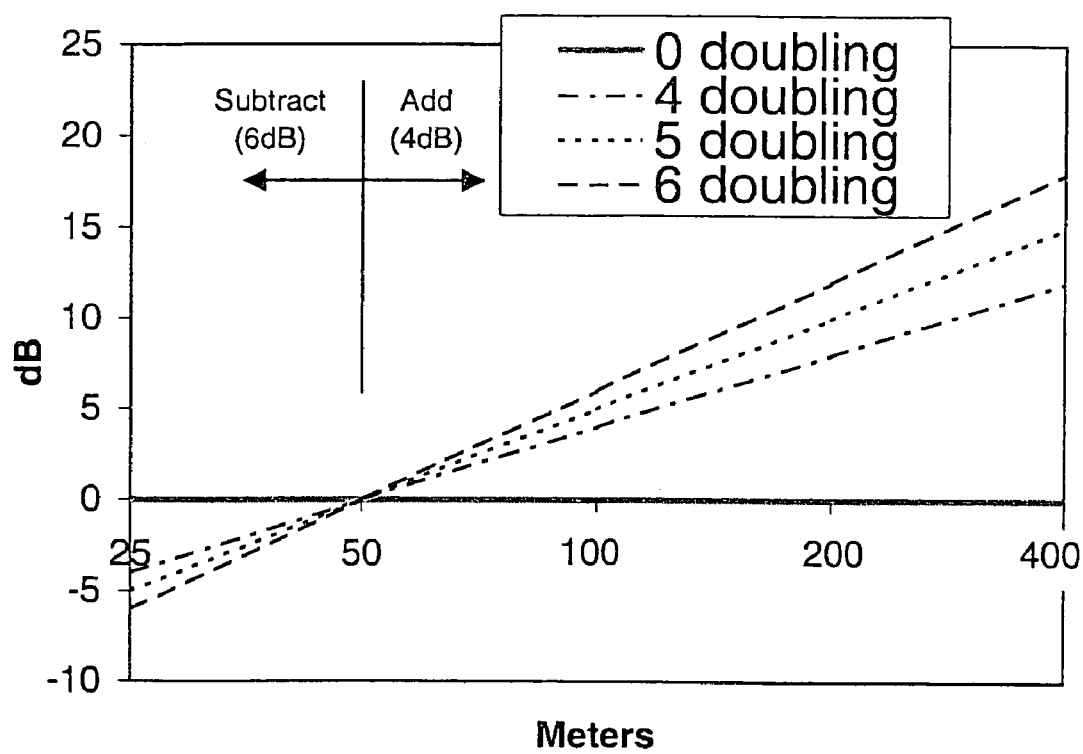
FIG. 6 is a sound level decay.
Figure 7:
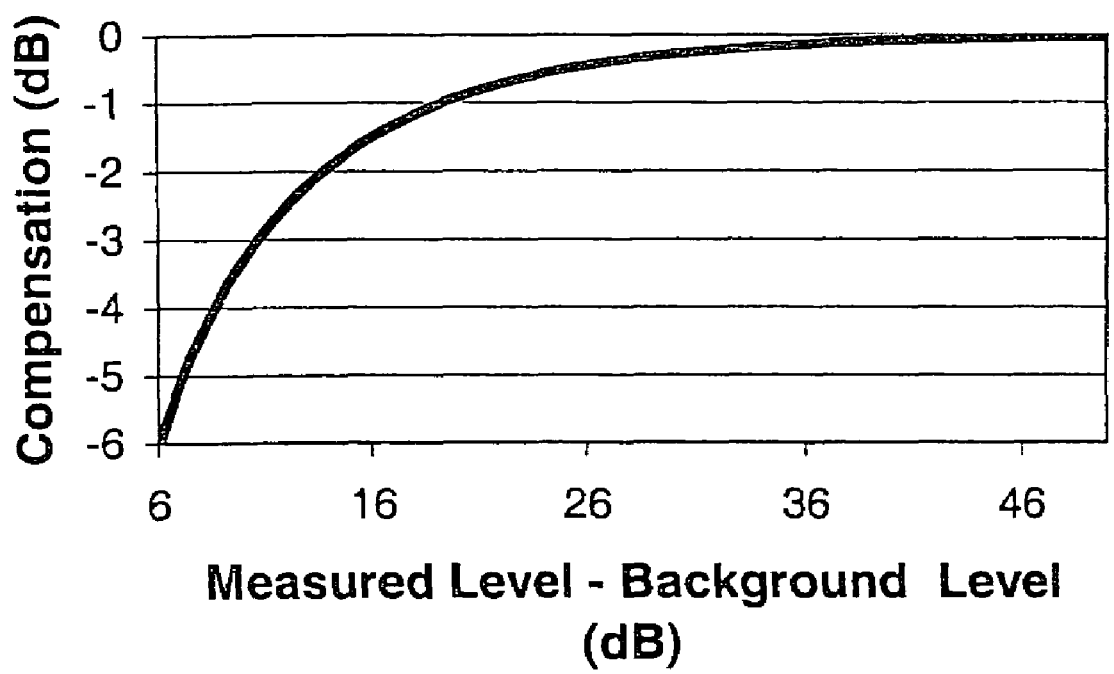
FIG. 7 is a sound level compensation C.
Figure 8:
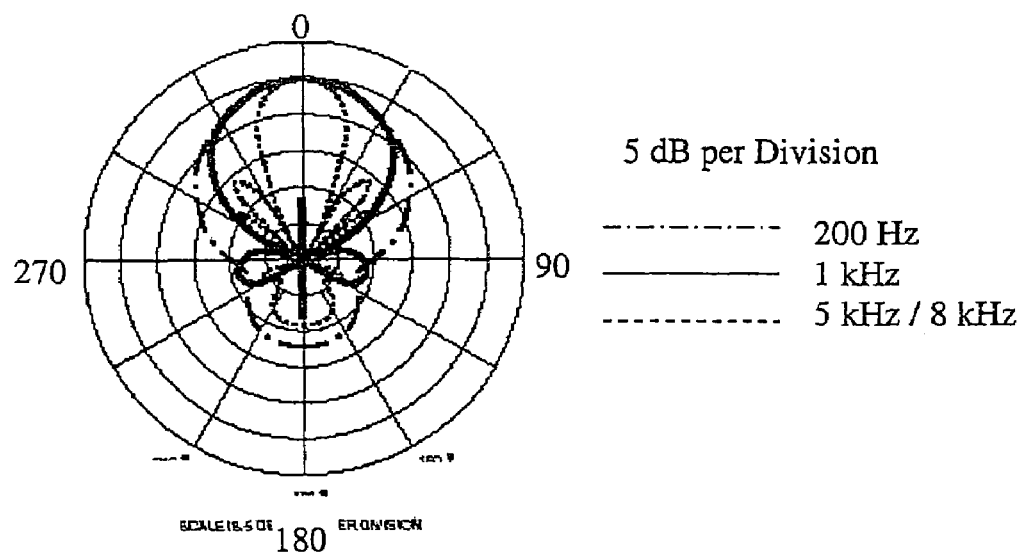
FIG. 8 is a polar response pattern of the Audio-Technica AT815b.

Shotgun microphone 34 uses a long tube that reinforces the sound wave as it travels both down the tube and on the outside of the tube. The length of the tube is important to increase the directionality of the microphone 34. However, the length does not play a direct role in the frequency response of the microphone. This type of microphone 34 provides 15-20 dB of directional discrimination. A response pattern for an Audio-Technica AT815b microphone is shown in FIG. 8.

For the directional sound measurement, shotgun microphone 34 was chosen. The parabolic microphone offered better directionality of sound measurement, at a cost of its large cross section. Shotgun microphone 34 offered only slightly inferior directionally of sound measurement and a much reduced cross-section. The length of the microphone 34 can also be reduced if less directionally at low frequencies is required.

The direct connection to microphone 34 is a balanced input. The output from microphone 34 is sent on two wires, and difference between the voltages on the wires is the microphone signal. The ground wire is kept separate to minimize noise pickup from magnetic/electric fields. The input is impedance balanced on each wire with the output impedance of microphone 34.

First op amp 44 is an inverting amplifier. The gain is determined as follows: First we record the fundamental laws of an op-amp $V^+ - V^- = 0$, which is a statement of the infinite gain of the amplifier, and $i_{in}^+ = i_{in}^- + 0$, which is a statement of the infinite input impedance of op amp 44.

The current through R2 is $$i_1 = (V_{in}^- - V_{out})/(R_1 + R_2) \quad (23)$$

and into the reference source, $$i_2 = (V_{in}^+ - V_{ref})/(R_3 + R_4) \quad (24)$$

Using the fundamental laws of an op amp, $$V^+ - V^- = [V_{in}^+ - R_3 i_2] - [V_{in}^- - R_1 i_1] = \quad (25)$$

Substituting the equations for $i_1$ and $i_2$ into the last equation, $$V^+ - V^- = 0 = [V_{in}^+ - R_3(V_{in}^+ - V_{ref})/(R_3 + R_4)] - [V_{in}^- - R_1(V_{in}^- - V_{out})/(R_1 + R_2)] \quad (26)$$

This result can be rearranged to form, $$V_{out} = \left(\frac{R_1}{R_1 + R_2}\right) - V_{ref}\left(\frac{R_3}{R_3 + R_4}\right) = V_{in}^+\left(\frac{R_4}{R_3 + R_4}\right) - V_{in}^-\left(\frac{R_2}{R_1 + R_2}\right) \quad (27)$$

If R1=R3 and R2=R4, $$(V_{out} - V_{ref}) = \left(\frac{R_2}{R_1}\right)(V_{in}^+ - V_{in}^-) \quad (28)$$

Equations 27 and 28 illustrate the importance of R1, R3 and R2, R4 being matched pairs. If these resistors are not equal the gain of the amplifier is not a simple ratio. The gain would be affected differently by changes in $V_{in}^+$ or $V_{in}^-$. Equation 28 defines the differential gain of the amplifier. Also note that this differential gain is defined about $V_{ref}$ because when $(V_{in}^+ - V_{in}^-) = 0$, $V_{out} = V_{ref}$, $V_{ref}$ as 2.5 V as required by the MX636 chip.

The input impedance of the circuit is the ratio between changes in each of the input voltages $V_{in}^+$ and $V_{in}^-$ and associated changes in currents $i_1$ and $i_2$. Using (25), $$V_{in}^+ = R_3 i_2 + V_{in}^- - R_3 i_1 \Rightarrow dV_{in}^+/di_1 = -R_3 \quad (29a)$$

and $$V_{in}^- = R_1 i_1 + V_{in}^+ - R_1 i_2 \Rightarrow dV_{in}^-/di_2 = -R_1 \quad (29b)$$

The input impedance of this amplifier is strictly controlled by the two identical input resistors $R_1$ and $R_3$. If $R_1 = 580$ Ohms, and $R_2 = 6.8$ k Ohms, the desired low microphone impedance with an amplifier gain is achieved, $(R_2/R_1) = 11.7$. With this gain, the RMS output voltage at a sound pressure level of 100 dB is (22.4 mV)*11.7=262.6 mV. Second op amp 46 is also an inverting amplifier, which a variable gain. This is used to trim the output to the exact requirements of the MX636.

The A/D stage measures the analog voltage and converts it into a digital representation of the value in terms of two limiting values. This digitally represented value is an 8-bit value. This is also a standard circuit. $R_1$ and $R_2$, and similarly $R_3$ and $R_4$, are voltage dividers, which define the limiting values.

$$V_3 = \frac{R_2}{R_1}(5 \text{ V}), \quad V_5 = \frac{R_4}{R_3}(2.5 \text{ V}) \quad (30)$$

V3 defines the bottom of the range of voltage, and V5 defines the span of voltages.

The digital output, x, is defined as $$x = \left(\frac{V_{in} - V\min}{V\text{span}}\right)255; \quad 0 \leq x \leq 255 \quad (31)$$

The ADC0831 provides x as the output of its serial interface. This serial output is a digitally scaled (0-255) RMS microphone level in dB.

When Vin=V3, x=0. When Vin=V3+V5, x =255.

Figure 13:
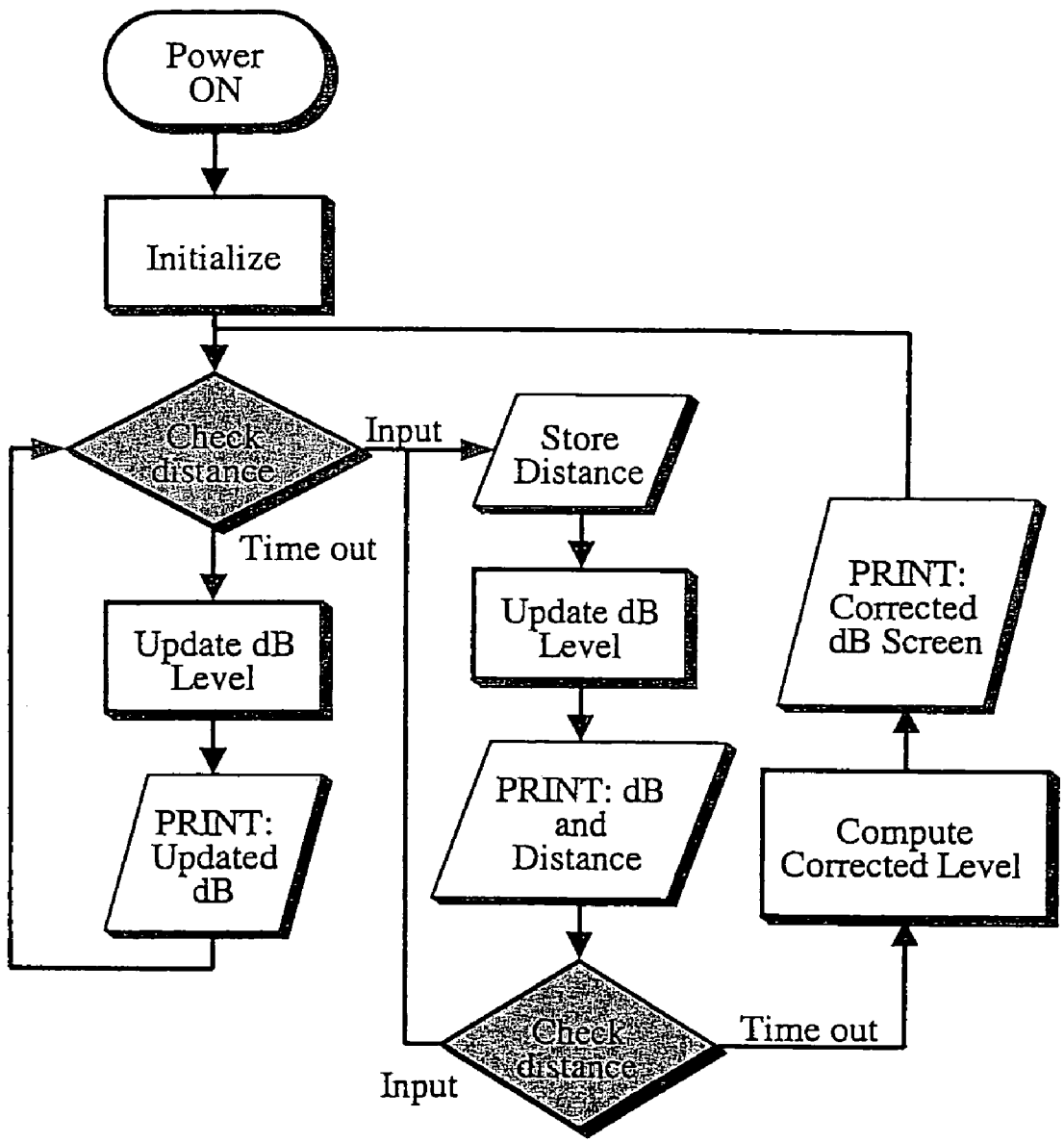
FIG. 13 is a flowchart of a program used in the sound measuring device shown in FIG. 9.
Figure 14:
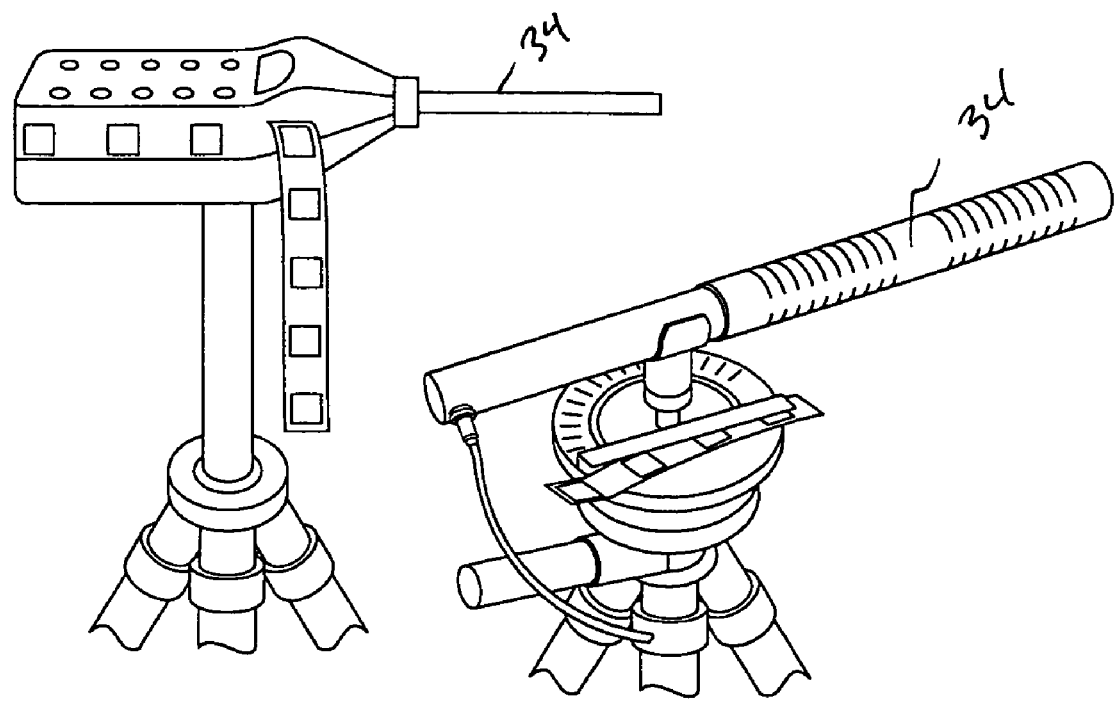
FIG. 14 is an anechoic chamber experimental setup.

Controller 36 converts the raw digital level from microphone 34, and computes an equivalent noise level at the measured distance. It computes a dB level from this number. Controller 36 then inputs the distance and computes a log correction to get the estimated noise equivalent noise level at a predetermined desired distance (50 feet). Controller 36 then uses the background noise and computes a reduction factor. This process is diagramed in FIG. 13.

In the initialization block, the device makes a measurement of the ambient sound level. It uses the microphone 34, amplifier 40, MX636, and A/D converter 42 stage to get a digital representation of the ambient sound level. The sound level data is inputted into basic stamp controller 36 as an 8-bit number, which is a representation of the decibel level at microphone 34. In order to overcome any noise on this 8-bit number, an infinite impulse response filter is used. This filter is used to obtain a 12-bit number by multiple sampling of the 8-bit output of the A/D converter. As long as the noise on the input is randomly distributed, this type of filter is accurate. The 12-bit number is converted into a dB value by interpolation. Since there is a linear relationship between the 12-bit number and the actual dB level at the microphone, tests are conducted to find this relationship. A lookup table is constructed to find the dB level from the 12-bit number.

In the first loop, sound measuring apparatus 30 uses the same noise sampling techniques to measure the noise value that the device is pointed at. It then gives a running display of this value and the background value. This is holding stage where the device is ready to make a calibrated measurement.

When the operator points device 30 at target boat 38 and pulls the trigger, controller 36 moves into the second loop. The device displays the distance to the target and the sound level in that direction updated continuously as long as the trigger is depressed. Upon the release of the trigger, controller 36 begins to make the corrections for ambient noise and distance to boat 38 or a moving sound generating target.

The ambient level correction is a logarithmic correction, and is pre-calculated for the difference between the background and the source. This log curve is then broken into linear segments, which the controller can make an interpolation between. The background noise level is stored in a memory location associated with the controller. As shown in the Sound Propagation Section, the background correction is:

$$C = 20\log_{10}(1 - 10^{[(Y_b - Y_m)/20]}) \quad (32)$$

The distance calculation is also a log correction. Controller 36 must know the log of the ratio of the distances in order to find the correction. However, in this case the log is calculated on the fly in the software. As shown in the sound propagation section, the SPL correction is:

$$\Delta SPL = 20\log_{10}\left(\frac{r_1}{r_2}\right) \quad (33)$$

The output of the device ($M_{corr}$) is thus the measured sound level (M), minus the corrections for ambient noise (C) and the corrections for distance (D).

$$M_{corr} = M - C - D \quad (34)$$

In calculating $M_{corr}$, the system can use a first correlation factor for noise from measure distances greater than the desired measurement distance, and a second correlation factor for noise from measured distances less than the desired measurement distance. As an example, the system can use a factor of 6 dB for measure distances greater than 25 m and 4 dB for less than 25 meters.

This value $M_{corr}$ is then displayed as an output in the final leg of the flowchart. It is displayed on a 3 digit 7-segment LED screen or an LCD screen. The sound measuring device holds at this point until the trigger is depressed again, which will move the device back into the first loop. At this point the whole process begins again.

Sound measuring device 30 was tested in an anechoic chamber. Since the directional sound measurement amplifies the boat noise, a calibration must be done to equate the level microphone 34 records with the actual dB level at the point of the observer. This calibration is done by comparing the microphone readings with standard B&K Type 2230 Microphone 34 readings in an environment with no reflections or other distortions of the sound propagation. This anechoic chamber has no reverberation below 30 Hz. The sound that hits the microphone is only from the source and not as reflections from any another surface. The Sound Source used was a B&K HP1001 at octave bands of 8 kHz, 4 kHz, 2 kHz, 1 kHz, 500 Hz, 250 Hz, 125 Hz, and for white noise.

Figure 15:
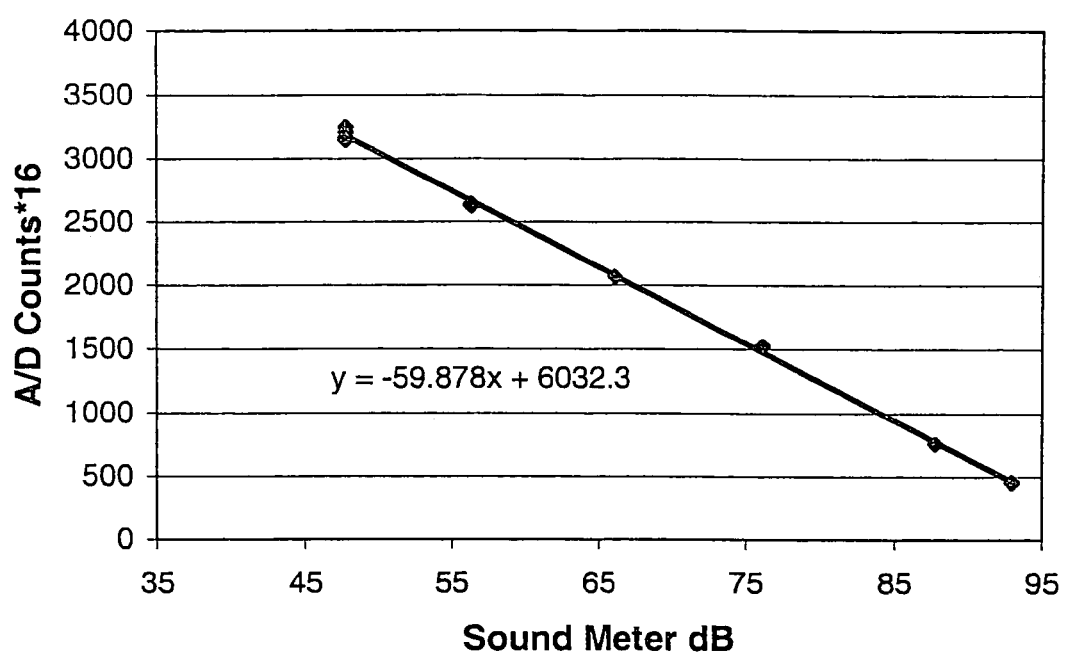
FIG. 15 is data from the first anechoic test for white noise.

The first test (FIG. 15) was performed to determine the correlation between what the sound measuring device read as the A/D conversion of the microphone data and the B&K dB level. At each sound level, four datapoints were taken. At each datapoint (App. F) the A/D measurement the sound measuring device made was recorded along with the B&K dB measurement. The data spreads at the lowest point, around 46 dB. At this level, the noise signal is probably too low for the sound measuring device to make an accurate measurement. Since sound measuring device 30 will never make a measurement of a boat at this low level, this data spread is not anticipated to cause problems. At higher dB levels, the four datapoints are almost exactly the same, so they appear as one dot on the graph and not four separate dots. A best fit line was developed from the data collected. This line fits the data from 46 dB to 94 dB with a maximum deviation of 87 counts. From this best fit, a lookup table was constructed for the sound measuring device. With this table, the sound measuring device could look up the dB value for a particular A/D measurement.

Figure 16:
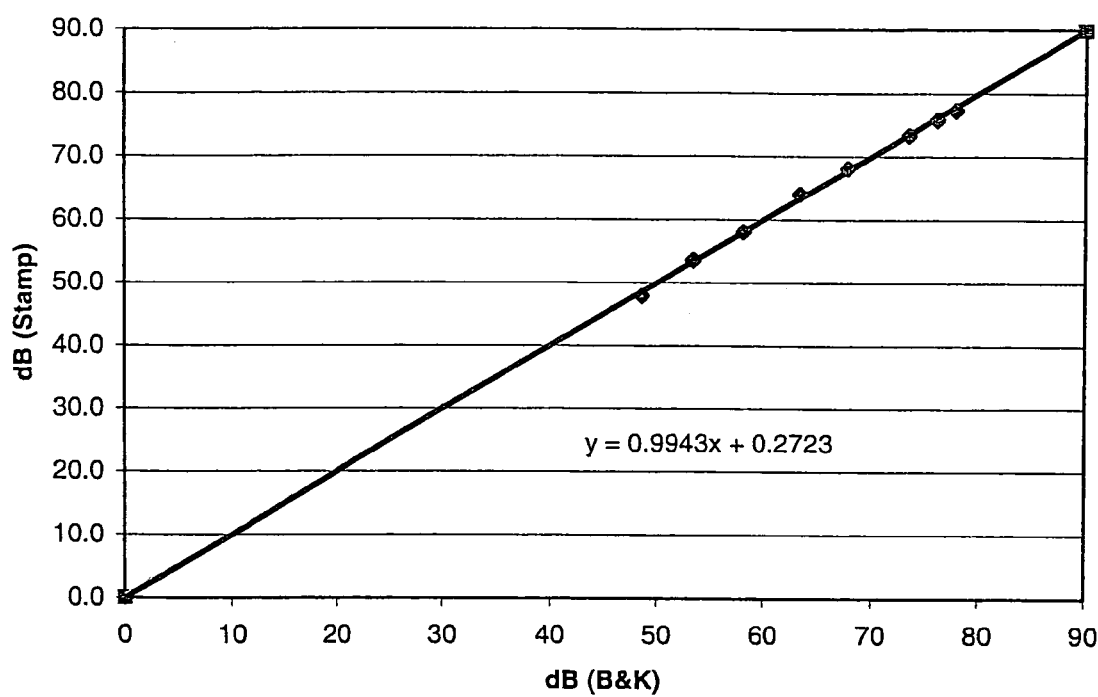
FIG. 16 is data from the second anechoic test for white noise.
Figure 17:
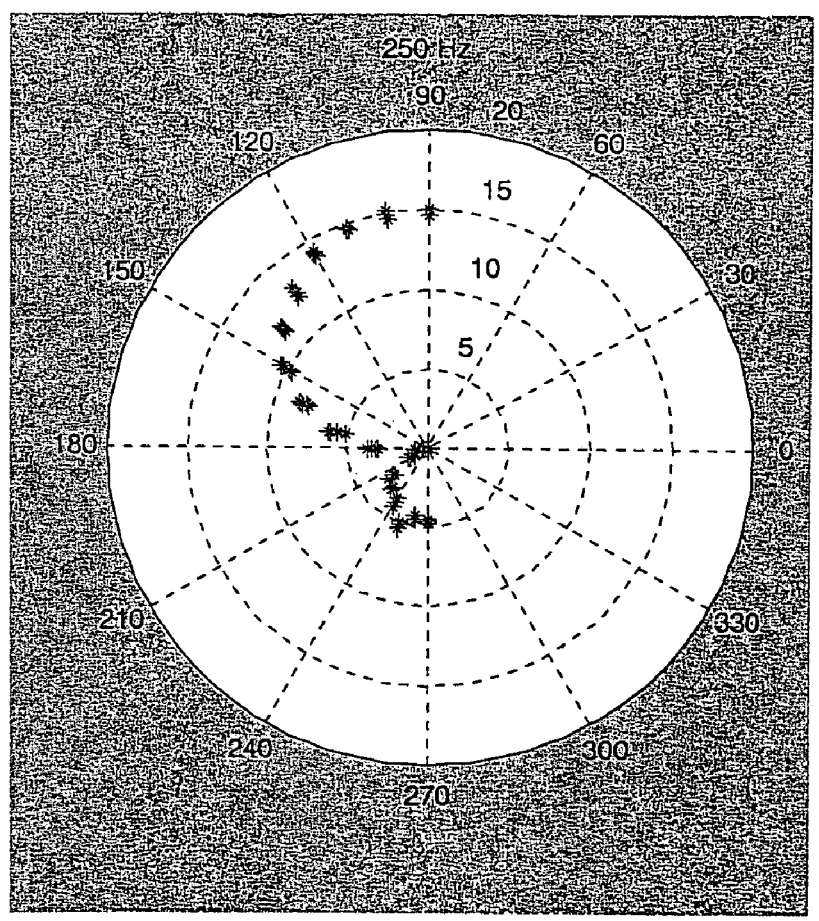
FIG. 17 is a polar response of (AT815-b) at 250 Hz octave band.

The second set of anechoic chamber testing (FIG. 16) compared the internal dB calculation with B&K readings to confirm the accuracy to the calibrated sound measuring device. At each sound level four datapoints were taken. Here the spread between datapoints is so small that they appear as 1 dot on the graph for a particular dB level. Ideally the line should have a slope of 1 and a intercept of 0. In this data the slope of the line is 0.99 and the intercept is 0.27. This second test proved that the lookup table between the sound measuring device and the B&K meter was accurate.

Tests were conducted to test the directionality of the microphone as listed in its data sheet. Tests were done in the anechoic chamber at octave bands of 8 kHz, 4 kHz, 2 kHz, 1 kHz, 500 Hz, 250 Hz, 125 Hz, and for white noise (App. F). The sound source was set and recorded at 78.1 dB, and the sound measuring device has a noise floor of 46 dB as shown previously. The total possible directionally that could have been found was 78.1 −46=32.1 dB. The specifications of microphone 34 claimed the directionality of the device at 25 dB, but this test showed a value of 15 dB. Since the sound measuring device can detect a gain of over 25 dB if it was present, the microphone characteristics must account for this difference. The radial shape pattern generally matches the manufacturer data.

Figure 18:
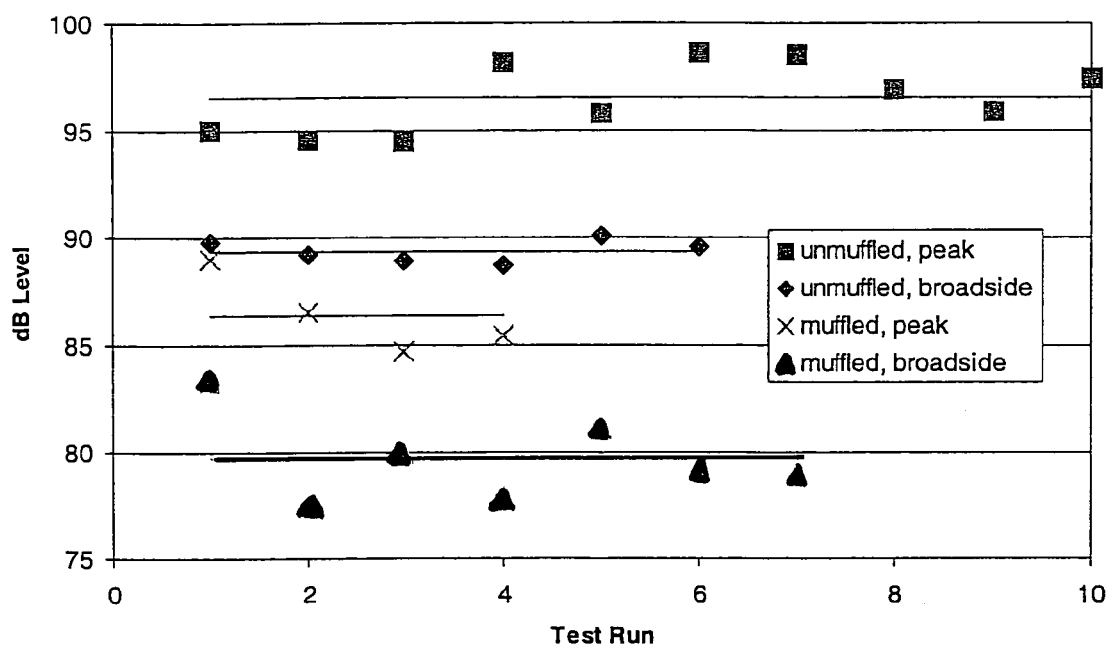
FIG. 18 is a summary of twenty-seven sound measuring device measurements.

Preliminary instrument testing was conducted on a local lake. A boat passed by the measurement location at approximately 40 mph to provide a consistent level of boat noise at various distances. Data recorded by the sound measuring device included a background noise measurement, directional raw noise measurement, distance measurement, and corrected noise measurement for each boat pass. One set of data was collected when boat 38 passed a line of premarked buoys perpendicular to the measurement location. This set of data is called broadside, because the side of boat 38 faced the observer. The second set of data was recorded after boat 38 had passed the buoys, when the sound measuring device operator subjectively determined that the boat noise level was at its peak. This set of data is called peak. Each set of data has two subsets, when the boat was running with and without its muffler turned on. These variables make four separate categories of boat runs. The data plotted in FIG. 18 is the corrected noise level for a standard distance of 50 feet that is computed by the sound measuring device with an assumption of 5 dB decay per doubling of distance. Full data records for these tests are in Appendix F.

The tests (FIG. 18) show that the boat's orientation relative to the observer and muffler condition are important to the results. For the unmuffled peak dataset, the mean is 96.5 dB and the standard deviation is 1.6 dB. For the muffled peak dataset, the mean is 86.7 dB and the standard deviation is 2.16 dB. For the unmuffled broadside dataset, the mean is 89.4 dB and the standard deviation is 0.54 dB. For the muffled broadside dataset, the mean is 79.5 dB and the standard deviation is 2.1 dB. In spite of 10-15 mph wind noise on the microphone, the device was able to make measurements over a wide range of distances with accuracy of better than +/-2 dB.

The dB decay for the doubling of distance $x_d$ used by the sound measuring device is variable, but can be set at 5 dB. This best estimate was derived from the NMMA study results. Since the exact optimal $x_d$ is unknown, this parameter for the test lake raw data was varied to determine the value of $x_d$ yielding the lowest standard deviation in the distance corrected data for each dataset. For each dataset, $x_d$ was varied from -3 to 9 dB and the standard deviation of each set was plotted. The lowest standard deviation for each dataset is the optimal decay rate $x_d$ for that test case. The best fit decay rate $x_d$ (FIG. 19) was different for each of four test cases. When the observer faced the broadside of the boat, the optimal $x_d$ was at about 4.5 dB (unmuffled) and 9 dB (muffled). When a peak measurement was taken, and the rear of the boat was visible to the observer, the data shows that the optimal $x_d$ was at about 1.5 dB (unmuffled), and at -0.7 dB (muffled). One hypothesis for these results is that the engine produces a plane wave coming off the back of the boat, and this wave spreads out around the corner of the boat. This would result in plane wave behavior observed from the back of the boat (peak measurement), and a spherical propagation pattern when viewing the side of the boat (broadside measurement).

The broadside vs. peak sound propagation pattern is shown by resolving the 4 cases into 2 cases. The RMS of the standard deviation of the peak cases is computed as $$SD_{peak} = \sqrt{\frac{(SD_{peak,muffled})^2 + (SD_{peak,unmuffled})^2}{2}} \quad (35)$$

Similarly for the broadside cases $$SD_{broadside} = \sqrt{\frac{(SD_{broadside,muffled})^2 + (SD_{broadside,unmuffled})^2}{2}} \quad (36)$$

Figure 19:
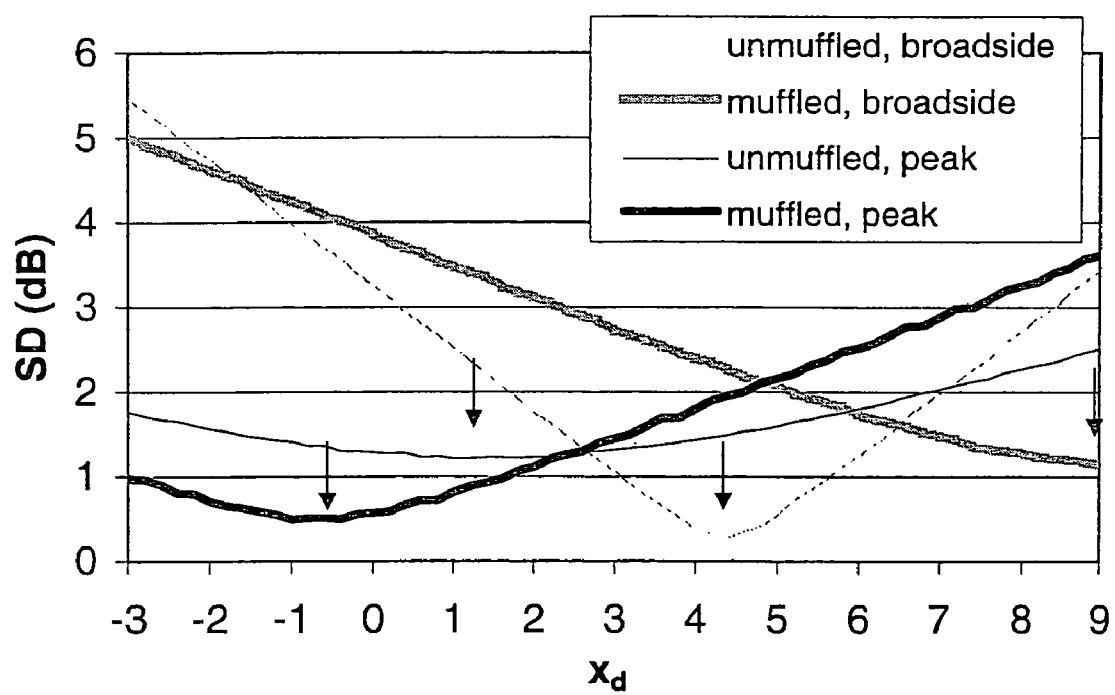
FIG. 19 is lake test data with the dB decay level altered.
Figure 20:
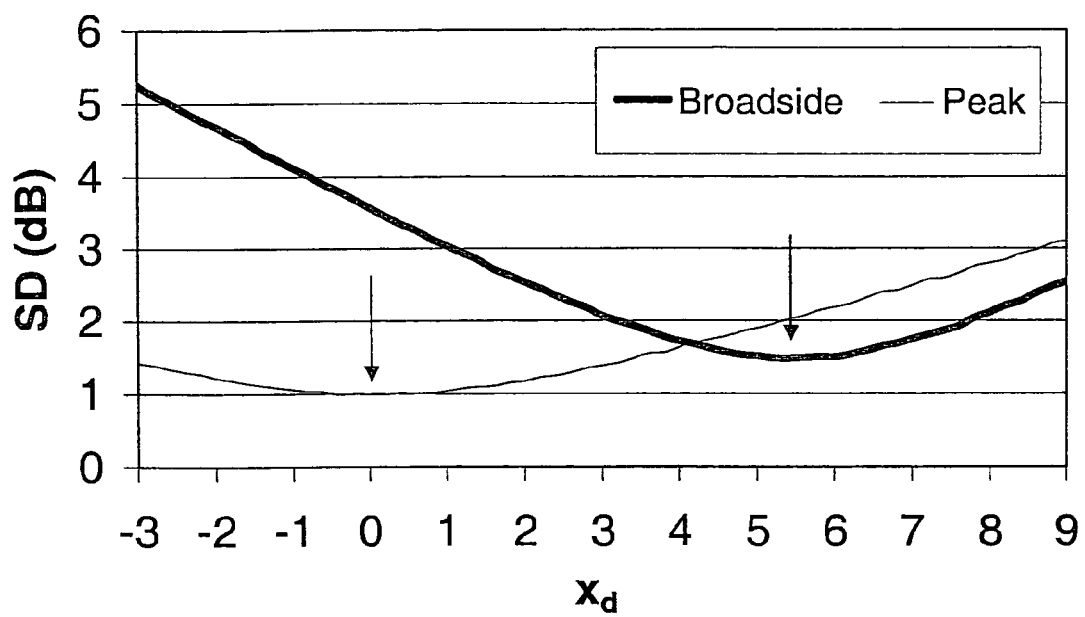
FIG. 20 is dB decay level altered for two cases.
Figure 21:
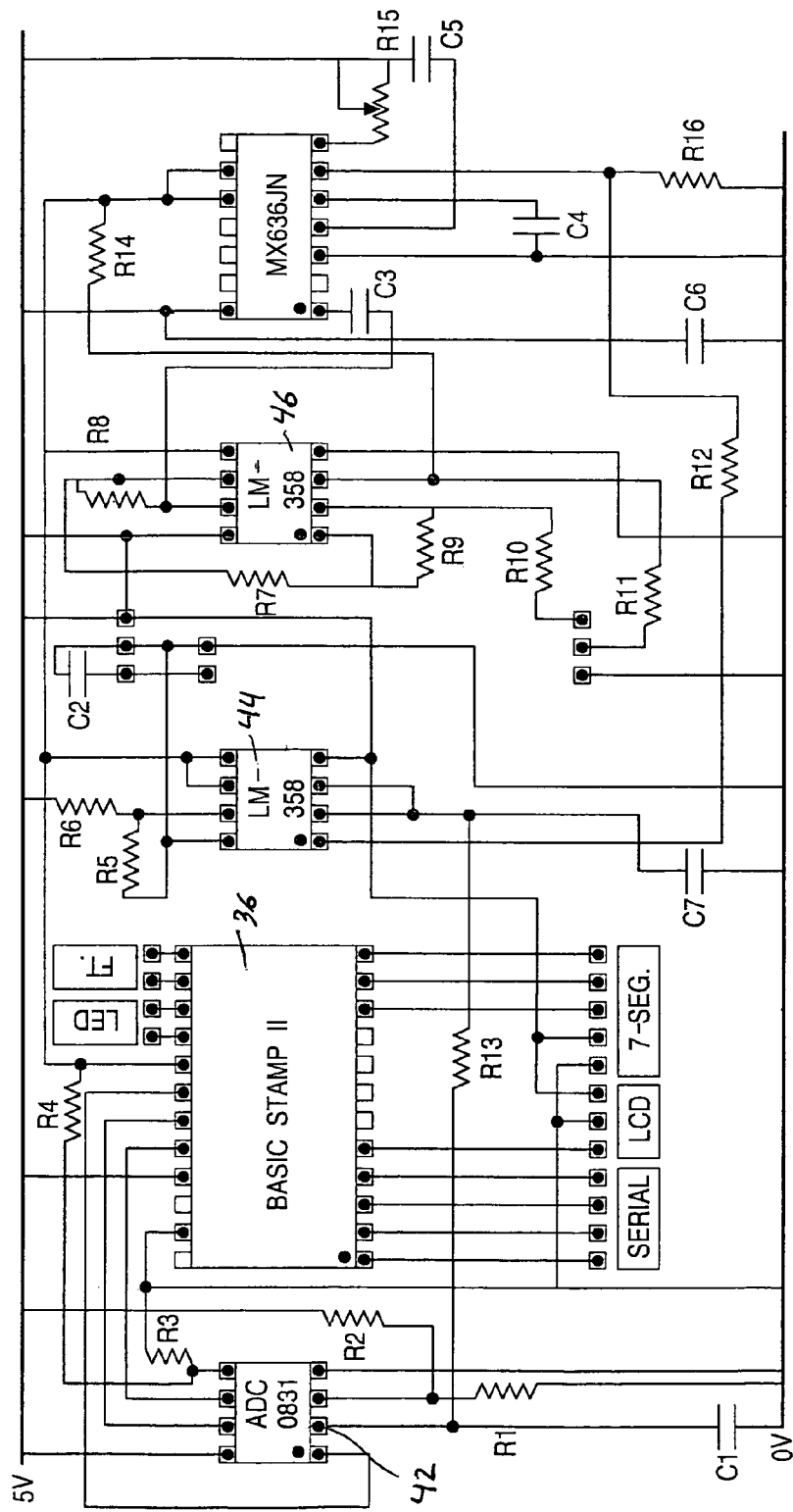
FIG. 21 is a circuit schematic diagram.
Figure 22:
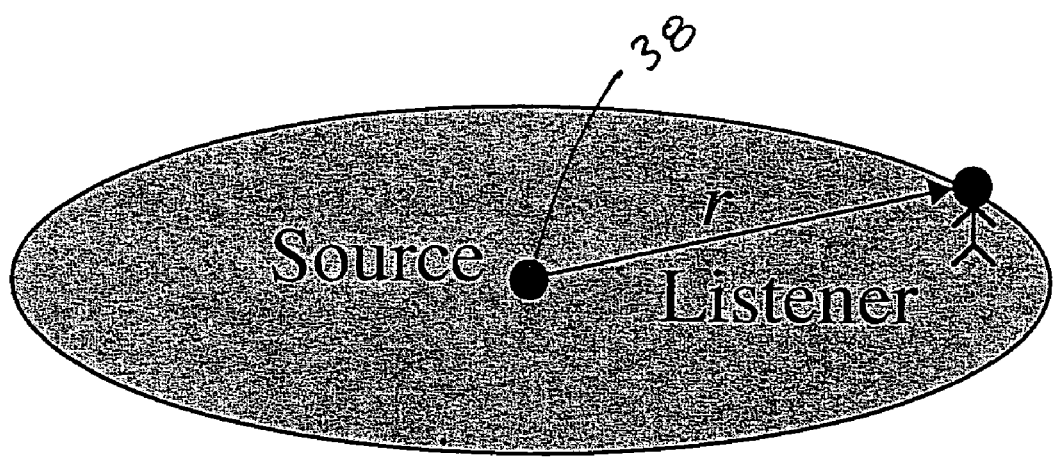
FIG. 22 is spherical sound propagation.
Figure 23:
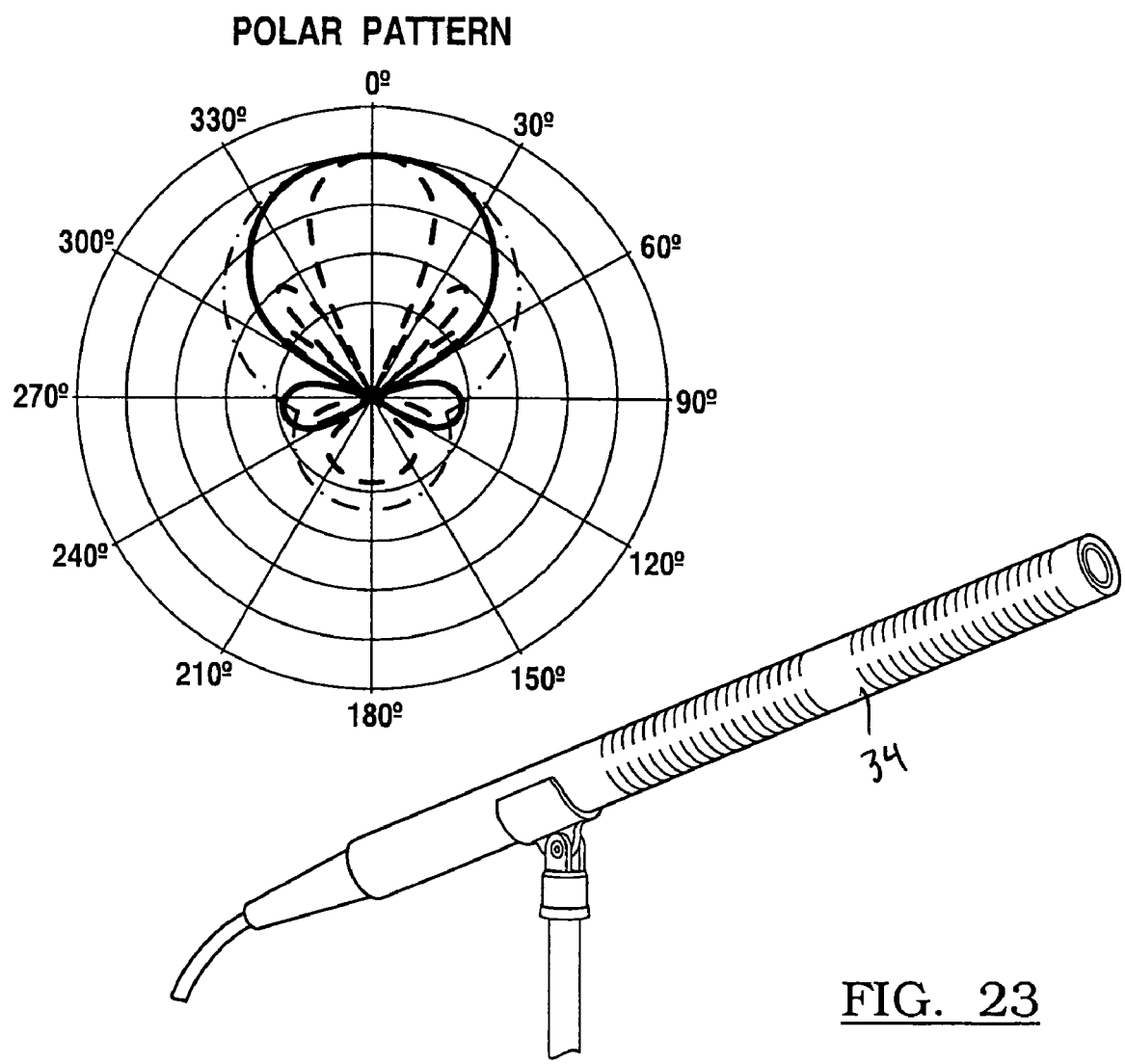
FIG. 23 is the Audio-Technica AT815b sound measuring device microphone.
Figure 24:
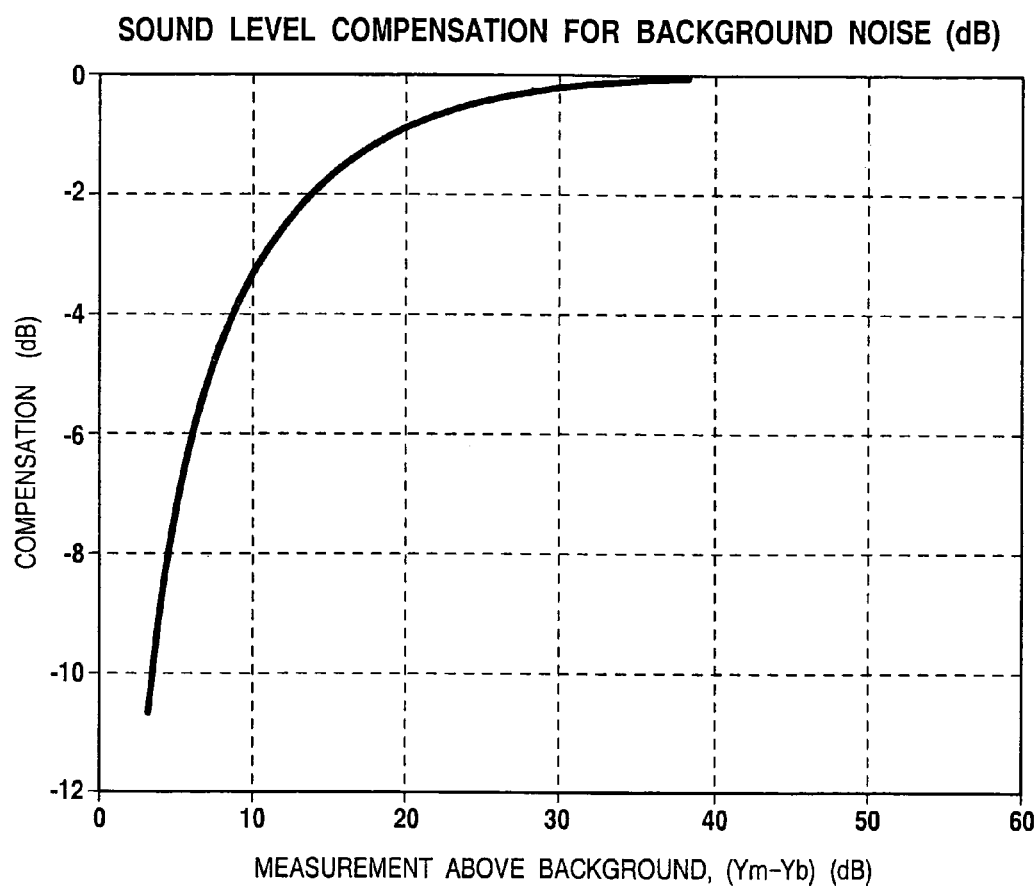
FIG. 24 is compensation C with known background level $Y_b$.

FIG. 19 confirms that the two cases are separate. For the Peak dataset, the ideal $x_d$ is very close to 0 dB. This correlates with plane waves. The Broadside dataset has an ideal $x_d$ of about 5.5 dB. This correlates well with the 6 dB of spherical propagation. More data needs to be taken to determine if there are only two cases or if the propagation pattern varies radially around the boat.

Sound detecting apparatus 30 meets the requirements of a directionally dependent noise measurement that is distance independent. The challenges of background and distance compensation have been solved, and these corrections have been implemented in a way that allows changes to be made easily. Functionally, sound detecting device 30 makes a background noise measurement, a directional noise measurement, and a distance measurement. From these three pieces of data it constructs an estimate of the loudness of boat 38 at a standard distance of 50 feet away (25 meters).

The propagation of sound affects changes to the design parameters of sound measuring device 30. If $x_d$ depends on orientation of the observer to boat 38, then that information would also have to be sensed for a distance correction to be made. If this difference can be resolved to a simple change between peak and broadside measurements, then a switch could be incorporated into the device to change the operational mode ($x_d$ of 0 or 6 dB). If the propagation pattern changes radially around the boat a measurement of the angle of the observer to the boat would have to be made. In any event, it is envisioned a device used by law enforcement could be configured to provide a displayed value of the minimum possible noise from a sound source, irrespective of propagation model, or sound detecting hardware used.

The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A sound detecting device comprising:
a controller;
a rangefinder configured to provide a distance signal indicative of a first distance from a noise producing target to the rangefinder and provide the signal to the controller;
a noise detector coupled to the controller; and
a display device configured to display a signal indicative of a measured noise from the target, wherein the sound detecting device is configured to measure noise from the noise producing target at about the first distance and provide an output which is an estimate of the noise level from the sound producing target at a second distance;
wherein the controller is configured to apply a first correction factor to a signal indicative of the measured noise if the first distance is less than the second distance, and a second correction factor if the first distance is at least the second distance.

2. The sound detecting device according to claim 1 wherein the rangefinder is a laser rangefinder.

3. The sound detecting device according to claim 1 wherein the rangefinder is a ultrasonic rangefinder.

4. The sound detecting device according to claim 1 wherein the second distance is about 25 meters.

5. The sound detecting device according to claim 1 wherein the noise detector is a microphone.

6. The sound detecting device according to claim 1 wherein the noise detector is a shotgun microphone.

7. The sound detecting device according to claim 1 wherein the noise detector is a parabolic microphone.

8. The sound detecting device according to claim 1 wherein the second distance is less than the first distance.

9. The sound detecting device according to claim 1 wherein the first distance is at least the second distance.

10. The sound detecting device according to claim 1 wherein the noise detecting device is configured to measure an ambient noise prior to measuring the noise from the target.

11. A sound detecting device configured to measure the transmitted noise from a moving object, the sound detecting device comprising:
a controller;
a rangefinder configured to provide a signal to the controller indicative of a first distance between the moving object and the sound detecting device; and
a microphone configured to provide a signal to the controller indicative of a level of noise coming from the moving object, wherein the controller is configured to provide an output indicative of an estimate of the noise which would be detected at a second distance from the moving object;
wherein the controller applies a first distance correction factor to a calculated noise level which is negative if the second distance is greater than the first, and the controller applies a second distance correction factor to a calculated noise level which is greater than zero if the second distance is less than the first distance.

12. The sound detecting device according to claim 11 wherein the second distance is at least the first distance.

13. The sound detecting device according to claim 11 wherein the first distance correction factor is based on a first propagation model and the second distance correction factor is based on a second propagation model.

14. The sound detecting device according to claim 11 wherein the controller calculates the minimum amount of possible noise from a source.

15. A sound detecting device configured to measure the transmitted noise from a moving object, the sound detecting device comprising:
a controller;
a rangefinder configured to provide a signal to the controller indicative of a first distance between the moving object and the sound detecting device; and
a microphone configured to provide a signal to the controller indicative of a level of noise coming from the moving object, wherein the controller is configured to provide an output indicative of an estimate of the noise which would be detected at a second distance from the moving object;
wherein the signal indicates a distance greater than 25 meters, the first distance correction factor is equivalent to about 4 dB per doubling of the measured distance and if the signal indicates a distance less than 25 meters, the second distance correction factor is 6 dB per doubling of measured distance.

16. A sound detecting device comprising:
a laser rangefinder configured to provide a signal indicative of a first distance between the rangefinder and a noise producing target;
a microphone configured to detect noise transmitted from the noise producing target at about the same time the rangefinder detects the distance to the target;
a display configured to display if the noise transmitted from the target is above a predetermined noise level;
a controller configured to accept the signals from the rangefinder and microphone and to calculate an estimate of the noise level which would be perceived from the noise producing target at a second distance from the noise producing target; and
wherein the controller is configured to subtract an ambient noise estimate from the detected noise.

17. The sound detecting device according to claim 16 further comprising an amplifier and an A/D converter operatively disposed between the microphone and the controller.

18. The sound detecting device according to claim 16 wherein the controller is configured to apply a first correction factor to the measured noise data if the first distance is less than the second distance and a second correction factor if the first distance is at least the second distance.

19. The sound detecting device according to claim 16 wherein the controller is configured to calculate the minimum amount of possible noise from a source at a predetermined distance from the source and sends a signal indicative thereof to the display.

20. A vibration detecting device comprising;
a mechanism configured to provide a signal indicative of a first distance between the mechanism and a vibration producing object;
a vibration detector configured to detect vibration transmitted from the vibration producing object at about the same time the mechanism detects the distance to the target;
a controller configured to accept the signals from the mechanism and vibration detector and to calculate an estimate of a vibration level which would be measured from the vibration producing object at a second distance from the vibration producing object; and
wherein the controller is configured to subtract an ambient vibration estimate from the detected vibration.

21. A method of determining an estimate noise level from a noise producing object at a predetermined distance from the object comprising the step of:
detecting a first distance from between a measuring device and the noise producing source;
detecting noise produced from the noise producing source;
measuring an ambient noise level;
producing a correction factor based on the ambient noise level;
calculating an estimate of a noise level which would be measured from the noise producing object at a second distance from the noise producing object; and
reducing the estimate of a noise level based on the correction factor.

* * * * *